United States Patent
Saito et al.

(10) Patent No.: US 9,347,056 B2
(45) Date of Patent: May 24, 2016

(54) NUCLEIC ACID EXTRACTION DEVICE, AND NUCLEIC ACID EXTRACTION METHOD, NUCLEIC ACID EXTRACTION KIT, AND NUCLEIC ACID EXTRACTION APPARATUS, EACH USING THE SAME

(71) Applicant: Seiko Epson Corporation, Tokyo (JP)

(72) Inventors: Yuji Saito, Shiojiri (JP); Fumio Takagi, Chino (JP)

(73) Assignee: Seiko Epson Corporation (JP)

( * ) Notice: Subject to any disclaimer, the term of this patent is extended or adjusted under 35 U.S.C. 154(b) by 112 days.

(21) Appl. No.: 14/062,228

(22) Filed: Oct. 24, 2013

(65) Prior Publication Data
US 2014/0120585 A1 May 1, 2014

(30) Foreign Application Priority Data

Oct. 26, 2012 (JP) ................. 2012-237068
Oct. 26, 2012 (JP) ................. 2012-237069

(51) Int. Cl.
*C12P 19/34* (2006.01)
*C12N 15/10* (2006.01)
(Continued)

(52) U.S. Cl.
CPC ............ *C12N 15/1013* (2013.01); *B01D 15/00* (2013.01); *B01L 3/50851* (2013.01); *B01L 3/50857* (2013.01); *C12N 15/1006* (2013.01); *C12N 15/1096* (2013.01); *G01N 30/6039* (2013.01); *G01N 30/6069* (2013.01); *G01N 30/6095* (2013.01); *B01D 15/1871* (2013.01); *B01D 15/22* (2013.01); *B01L 2200/0647* (2013.01); *B01L 2200/0673* (2013.01); *B01L 2200/16* (2013.01); *B01L 2300/0838* (2013.01);
(Continued)

(58) Field of Classification Search
None
See application file for complete search history.

(56) References Cited

U.S. PATENT DOCUMENTS 8,048,633 B2  11/2011  Collier et al.
8,187,808 B2   5/2012  Kelso et al.
(Continued)

FOREIGN PATENT DOCUMENTS

EP   1 502 951 A1   2/2005
JP   2005-503572 A  2/2005
(Continued)

OTHER PUBLICATIONS

Boom, R. et al., "Rapid and Simple Method for Purification of Nucleic Acids", Journal of Clinical Microbiology, vol. 28, No. 3, pp. 495-503, 1990.
(Continued)

*Primary Examiner* — Kenneth Horlick
(74) *Attorney, Agent, or Firm* — Harness, Dickey & Pierce, P.L.C.

(57) ABSTRACT

A nucleic acid extraction device includes a tube that is internally provided with, in the following order, a first plug composed of a first oil, a second plug composed of a first washing liquid, which is phase-separated from an oil and is used for washing a nucleic acid-binding solid-phase carrier having nucleic acids bound thereto, a third plug composed of a second oil, a fourth plug composed of a reverse transcription reaction solution, which is phase-separated from an oil and is used for performing a reverse transcription reaction, a fifth plug composed of a third oil, a sixth plug composed of an eluent, which is phase-separated from an oil and is used for eluting the nucleic acids from the nucleic acid-binding solid-phase carrier having nucleic acids bound thereto, and a seventh plug composed of a fourth oil.

20 Claims, 6 Drawing Sheets

(51) Int. Cl.
*B01D 15/00* (2006.01)
*G01N 30/60* (2006.01)
*B01L 3/00* (2006.01)
*B01D 15/18* (2006.01)
*B01D 15/22* (2006.01)
*G01N 30/00* (2006.01)

(52) U.S. Cl.
CPC ..... *B01L 2400/043* (2013.01); *G01N 2030/009* (2013.01)

(56) References Cited

U.S. PATENT DOCUMENTS

| | | |
|---|---|---|
| 2004/0161788 A1 | 8/2004 | Chen et al. |
| 2004/0241693 A1 | 12/2004 | Ricoul et al. |
| 2010/0092973 A1* | 4/2010 | Davies et al. ............... 435/6 |
| 2011/0236960 A1 | 9/2011 | Bird et al. |
| 2012/0190033 A1* | 7/2012 | Ness et al. ................ 435/6.12 |

FOREIGN PATENT DOCUMENTS

| | | |
|---|---|---|
| JP | 2008-012490 A | 1/2008 |
| JP | 2008-525037 A | 7/2008 |
| JP | 2009-207459 A | 9/2009 |
| JP | 2011-516034 A | 5/2011 |
| JP | 2012-251805 A | 12/2012 |
| WO | WO-95-28409 A1 | 10/1995 |
| WO | WO-96-09308 A1 | 3/1996 |

OTHER PUBLICATIONS

Extended European Search Report for Application No. EP 13 19 0250 dated Jan. 23, 2014 (5 pages).

* cited by examiner

NUCLEIC ACID EXTRACTION DEVICE, AND NUCLEIC ACID EXTRACTION METHOD, NUCLEIC ACID EXTRACTION KIT, AND NUCLEIC ACID EXTRACTION APPARATUS, EACH USING THE SAME

BACKGROUND

1. Technical Field

The present invention relates to a nucleic acid extraction device, and a nucleic acid extraction method, a nucleic acid extraction kit, and a nucleic acid extraction apparatus, each using the same.

2. Related Art

Boom et al. have reported a method for more easily extracting nucleic acids from a biomaterial using a nucleic acid-binding solid-phase carrier such as silica particles and a chaotropic agent (see J. Clin. Microbiol., vol. 28, No. 3, pp. 495-503 (1990)). A method for extracting nucleic acids using a nucleic acid-binding solid-phase carrier such as silica and a chaotropic agent by adsorbing nucleic acids on the carrier including this method of Boom et al. mainly includes the following three steps: (1) a step of adsorbing nucleic acids on a nucleic acid-binding solid-phase carrier in the presence of a chaotropic agent (adsorption step); (2) a step of washing the carrier having nucleic acids adsorbed thereon with a washing liquid for removing nonspecifically bound foreign substances and the chaotropic agent (washing step); and (3) a step of eluting the nucleic acids from the carrier using water or a low salt concentration buffer (elution step).

SUMMARY

An advantage of some aspects of the invention is to provide a novel nucleic acid extraction device, and a nucleic acid extraction method, a nucleic acid extraction kit, and a nucleic acid extraction apparatus, each using the same.

An aspect of the invention is directed to a nucleic acid extraction device including a tube that is internally provided with, in the following order, a first plug composed of a first oil, a second plug composed of a first washing liquid, which is phase-separated from an oil and is used for washing a nucleic acid-binding solid-phase carrier having nucleic acids bound thereto, a third plug composed of a second oil, a fourth plug composed of a reverse transcription reaction solution, which is phase-separated from an oil and is used for performing a reverse transcription reaction, a fifth plug composed of a third oil, a sixth plug composed of an eluent, which is phase-separated from an oil and is used for eluting the nucleic acids from the nucleic acid-binding solid-phase carrier having nucleic acids bound thereto, and a seventh plug composed of a fourth oil. The tube may be further provided with, between the fifth plug and the sixth plug in order from the fifth plug side, a tenth plug composed of a second washing liquid, which is phase-separated from an oil and is used for washing the nucleic acid-binding solid-phase carrier having nucleic acids bound thereto, and an eleventh plug composed of an oil. The eluent may contain a DNA polymerase, dNTP, and a primer for the DNA polymerase. The end of the tube on the seventh plug side is an open end which is open, and the tube may have a detachable stopper which seals the open end. The device may further include a tank for introducing the nucleic acid-binding solid-phase carrier into the tube. The tank and the tube may be detachable from each other. The tank may contain a lysis solution for lysing a sample from which nucleic acids are extracted.

Another aspect of the invention is directed to a nucleic acid extraction method including: disposing the above-described nucleic acid extraction device, in which the eluent is contained in the tank, such that the longitudinal direction of the tube is parallel with the gravitational direction; feeding a sample from which RNA is extracted to the tank; applying a magnetic force to the tube in the direction from the first plug to the fourth plug to move a magnetic material from the inside of the tank to the fourth plug; reverse transcribing the RNA in the reverse transcription reaction solution of the fourth plug to synthesize cDNA; and releasing the cDNA from the nucleic acid-binding solid-phase carrier in the eluent of the sixth plug.

Still another aspect of the invention is directed to a nucleic acid extraction kit including: the above-described nucleic acid extraction device; a nucleic acid-binding solid-phase carrier having a magnetic material; and a lysis solution for lysing a sample from which nucleic acids are extracted.

Yet still another aspect of the invention is directed to a nucleic acid extraction apparatus including: a nucleic acid extraction device, which includes a tube that is internally provided with, in the following order, a first plug composed of a first oil, a second plug composed of a first washing liquid, which is phase-separated from an oil and is used for washing a nucleic acid-binding solid-phase carrier having nucleic acids bound thereto, a third plug composed of a second oil, a fourth plug composed of a reverse transcription reaction solution, which is phase-separated from an oil and is used for performing a reverse transcription reaction; a fifth plug composed of a third oil, a sixth plug composed of an eluent, which is phase-separated from an oil and is used for eluting the nucleic acids from the nucleic acid-binding solid-phase carrier having nucleic acids bound thereto, and a seventh plug composed of a fourth oil; and a magnetic force application device that applies a magnetic force to the tube. The nucleic acid extraction apparatus may further include a magnetic force application device moving unit or a nucleic acid extraction device moving unit, each of which relatively changes a positional relationship between the tube and the magnetic force application device along the longitudinal direction of the tube. The nucleic acid extraction apparatus may further include a heating unit which is disposed at a position where the unit heats the fourth plug and/or the sixth plug of the tube. The tube may be provided with, between the fifth plug and the sixth plug in order from the fifth plug side, a tenth plug composed of a second washing liquid, which is phase-separated from an oil and is used for washing the nucleic acid-binding solid-phase carrier having nucleic acids bound thereto, and an eleventh plug composed of an oil. The eluent may contain a DNA polymerase, dNTP, and a primer for the DNA polymerase. The end of the tube on the seventh plug side may be an open end which is open, and the tube may have a detachable stopper which seals the open end. The apparatus may further include a tank for introducing the nucleic acid-binding solid-phase carrier into the tube. The tank may contain a lysis solution for lysing a sample from which nucleic acids are extracted.

According to the aspects of the invention, it becomes possible to provide a novel nucleic acid extraction device, and a nucleic acid extraction method, a nucleic acid extraction kit, and a nucleic acid extraction apparatus, each using the same.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

Figure 1A:
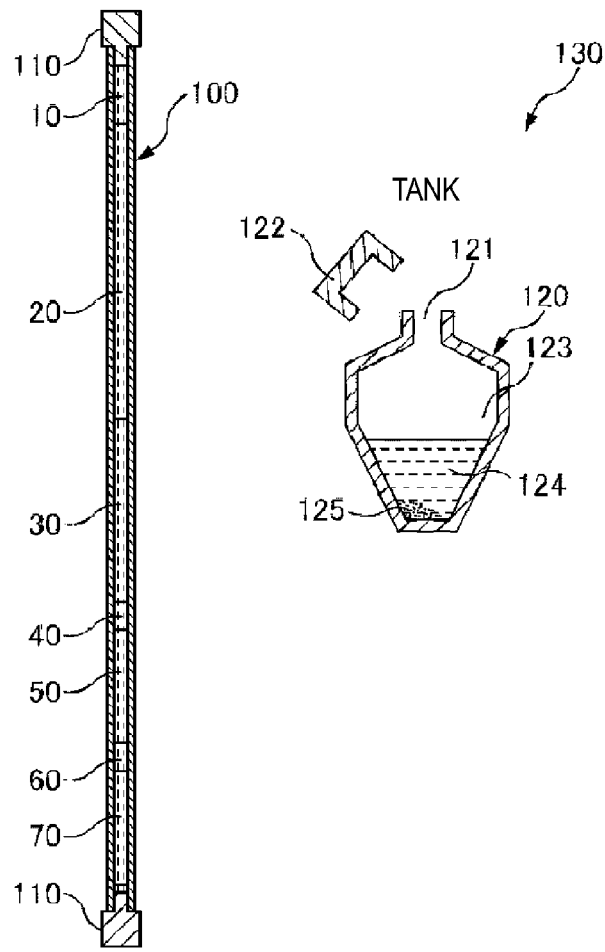
FIGS. 1A and 1B are schematic views each showing a structure of a nucleic acid extraction device according to an embodiment of the invention.

Unless otherwise specifically stated in the embodiments and examples, the methods described in standard protocols such as M. R. Green & J. Sambrook (Ed.), Molecular cloning, a laboratory manual (4th edition), Cold Spring Harbor Press, Cold Spring Harbor, N.Y. (2012); F. M. Ausubel, R. Brent, R. E. Kingston, D. D. Moore, J. G. Seidman, J. A. Smith, K. Struhl (Ed.), and Current Protocols in Molecular Biology, John Wiley & Sons Ltd., or modified or altered methods thereof are used. Further, when commercially available reagents, kits, or measurement devices are used, unless otherwise specifically stated, the protocols attached thereto are used.

The objects, features, advantages, and ideas of the invention will be apparent to those skilled in the art from the description of this specification, and those skilled in the art can easily reproduce the invention from the description of this specification. The modes, specific examples, etc. of the invention described below represent preferred embodiments of the invention, which are given for the purpose of illustration or description, and the invention is not limited thereto. Those skilled in the art may recognize that various modifications and changes may be made based on the description of the specification without departing from the spirit and scope of the invention disclosed herein.

Nucleic Acid Extraction Device (1) Tank

The nucleic acid extraction device according to an embodiment of the invention includes a tank for introducing a nucleic acid-binding solid-phase carrier into a single tube or a plurality of tubes.

The tank can contain a liquid therein, and has an opening capable of introducing a substance into the tank from the outside. The position of the opening in the tank is not particularly limited and the tank may have a plurality of openings. The opening may have a detachable cap.

The internal volume of the tank is not particularly limited, but can be set to, for example, 0.1 mL or more and 100 mL or less. A material for the tank is not particularly limited, but for example, a glass, a resin such as a plastic, a metal, or the like can be used. In particular, when a transparent glass or resin is selected as the material for the tank, the inside of the tank can be observed from the outside, and thus, such a material is more preferred. It does not matter whether the tank and each tube are integrally formed or detachably formed. When a flexible material such as a rubber, an elastomer, or a polymer is used as a material for the tank, it is possible to apply pressure to the inside of the tank by deforming the tank in a state where the cap is attached to the tank. By doing this, the content of the tube can be ejected from the end of the tube to the outside from the inside of the tube.

The tank preferably contains a lysis solution for lysing a sample from which nucleic acids are extracted, and the tank can be shaken together with the tube and the liquid in the tank can be sufficiently stirred.

The lysis solution is not particularly limited as long as it contains a chaotropic substance, but a surfactant may be incorporated therein for the purpose of disrupting cell membranes or denaturing proteins contained in cells. This surfactant is not particularly limited as long as it is generally used for extracting nucleic acids from cells or the like. Specific examples thereof include nonionic surfactants such as Triton surfactants (such as Triton-X) and Tween surfactants (such as Tween 20) and anionic surfactants such as sodium n-lauroyl-sarcosinate (SDS). However, particularly, it is preferred to use a nonionic surfactant in an amount ranging from 0.1 to 2%. Further, the lysis solution preferably contains a reducing agent such as 2-mercaptoethanol or dithiothreitol. The lysis solution may be a buffer, but preferably has a neutral pH ranging from 6 to 8. In view of this, specifically, the lysis solution preferably contains a guanidine salt (3 to 7 M), a nonionic surfactant (0 to 5%), EDTA (0 to 0.2 mM), a reducing agent (0 to 0.2 M), etc.

The chaotropic substance is not particularly limited as long as it generates a chaotropic ion (a monovalent anion having a large ionic radius) in an aqueous solution, has an activity to increase the water solubility of a hydrophobic molecule, and contributes to the adsorption of nucleic acids on the solid-phase carrier. Specific examples thereof include guanidine thiocyanate, guanidine hydrochloride, sodium iodide, potassium iodide, and sodium perchlorate. Among these, guanidine thiocyanate or guanidine hydrochloride having a high protein denaturation activity is preferred. The used concentration of such a chaotropic substance varies depending on the respective substances, and for example, when guanidine thiocyanate is used, the used concentration thereof is preferably in a range of 3 to 5.5 M, and when guanidine hydrochloride is used, the used concentration thereof is preferably 5 M or more.

When the tube is disposed in parallel with the gravitational direction, the tank is configured to be disposed above the tube. A sample is placed in the tank, followed by shaking, and thereafter, the tube is disposed in parallel with the gravitational direction again. Although the tank contains the lysis solution, it is preferred that a space is left in the tank. This is because, if so, by merely lightly shaking this nucleic acid extraction device, for example, by turning the device upside down, the liquid in the tank can be easily mixed.

In the case where the nucleic acid extraction device includes a plurality of tubes, when the tubes are disposed in parallel with the gravitational direction, the tubes are configured to all line up in parallel with one another at the same level. The tank is provided with a liquid dispensing section which dispenses a liquid containing a nucleic acid-binding solid-phase carrier to each tube, and is configured such that when a liquid containing a nucleic acid-binding solid-phase carrier is placed in the tank, the liquid is dispensed along with the nucleic acid-binding solid-phase carrier by the liquid dispensing section, and the nucleic acid-binding solid-phase carrier is introduced into each tube through the liquid. The liquid dispensing section may have a partition wall which separates spaces communicating to the respective tubes. By this partition wall, the bottom surface of the tank continuing to the respective tubes can be separated with respect to each tube. The bottom surface extends perpendicularly to the gravitational direction, and if the partition wall is perpendicular to the bottom surface, the ratio of the area of the bottom surface connected to each tube coincides with the ratio of the amount of the nucleic acid-binding solid-phase carrier dispensed to each tube. For example, if the areas of the bottom surfaces connected to the respective tubes are equal, the nucleic acid-binding solid-phase carrier is equally dispensed to the respective tubes. When a sample is placed in the tank, followed by shaking, and thereafter, the tubes are disposed in parallel with the gravitational direction again, the liquid level in the tank can be raised above the partition wall in this disposition state. In this manner, the liquid can be allowed to uniformly flow into the plurality of tubes.

The nucleic acid-binding solid-phase carrier is not particularly limited as long as it is a solid having a hydrophilic surface capable of adsorbing nucleic acids, in other words, retaining nucleic acids through a reversible physical bond in the presence of a chaotropic ion. Specifically, a substance containing silicon dioxide, for example, silica, glass, diatomaceous earth, or a substance obtained by subjecting such a substance to a surface treatment by chemical modification is preferred, and a complex thereof with a magnetic material, a superparamagnetic metal oxide, or the like is more preferred. In the case where a surface treatment by chemical modification is performed, the substance may be moderately charged with positive electricity to such an extent that it does not inhibit the reversible bond with nucleic acids.

Examples of the form of the nucleic acid-binding solid-phase carrier include a block, a particle, and a powder, but it is not limited thereto. Among these, the particle form is more preferred in view of efficiency of adsorption and elution. In this case, the particle diameter is not particularly limited, but may be from 0.05 to 500 μm, and is preferably from 1 to 100 μm, and particularly preferably from 1 to 10 μm.

It is preferred that the nucleic acid-binding solid-phase carrier has a density larger than the lysis solution. For example, if the density of the lysis solution is from 1.1 to 1.2 g/mL, the density of the nucleic acid-binding solid-phase carrier may be set to, for example, 1.5 to 2.0 g/mL.

(2) Tube

The nucleic acid extraction device according to the embodiment of the invention includes a tube that is internally provided with, in the following order, a first plug composed of a first oil, a second plug composed of a first washing liquid, which is phase-separated from an oil and is used for washing a nucleic acid-binding solid-phase carrier having nucleic acids bound thereto, a third plug composed of a second oil, a fourth plug composed of a reverse transcription reaction solution, which is phase-separated from an oil and is used for performing a reverse transcription reaction, a fifth plug composed of a third oil, a sixth plug composed of an eluent, which is phase-separated from an oil and is used for eluting the nucleic acids from the nucleic acid-binding solid-phase carrier having nucleic acids bound thereto, and a seventh plug composed of a fourth oil. The nucleic acid extraction device may include a plurality of tubes. In the case where the nucleic acid extraction device includes a plurality of tubes, it does not matter whether the tubes are entirely arranged linearly or circularly as long as they are arranged in parallel with one another. The linear arrangement facilitates the simultaneous control of all of the plurality of tubes, and the circular arrangement enables the reduction in size of the entire device. Here, the plug refers to a liquid in the case where one type of liquid makes up one section in the tube.

The tube has a hollow interior portion and has a cylindrical shape capable of allowing a liquid to flow through the tube in the longitudinal direction, and may be called a "capillary". The tube may be bent in the longitudinal direction but is preferably linear. The size and shape of the hollow interior portion of the tube are not particularly limited as long as a liquid can be maintained to have the shape of a plug in the tube. The size of the hollow interior portion of the tube or the shape of the cross section perpendicular to the longitudinal direction thereof are preferably constant in the longitudinal direction of the tube, but may vary.

The shape of the cross section perpendicular to the longitudinal direction of the contour of the tube is also not limited, but is preferably a circle or an ellipse close to a circle. The thickness (the length from the side surface of the hollow interior portion to the outer surface) of the tube is also not particularly limited, but is preferably uniform. In the case where the tube has a cylindrical shape, the inner diameter (the diameter of a circle of the cross section perpendicular to the longitudinal direction of the hollow interior portion) thereof can be set to, for example, 0.5 mm or more and 3 mm or less. If the inner diameter of the tube is within this range, the plug composed of a liquid is easily formed within a wide range of the material for the tube and the type of the liquid.

The material for the tube is not particularly limited, and for example, a glass, a resin such as a plastic, a metal, or the like can be used. In particular, when a transparent glass or resin is selected as the material for the tube, the hollow interior portion can be observed from the outside of the tube, and thus, such a material is more preferred. Alternatively, when a substance through which a magnetic force is transmitted or a non-magnetic material is selected as the material for the tube, in the case where magnetic particles are allowed to pass through the tube or the like, by applying a magnetic force from the outside of the tube, the magnetic particles can be easily allowed to pass through the tube, and thus, such a material is preferred. Further, as the material for the tube, the same material as that for the tank may be used.

The end of the tube on the seventh plug side may be an open end which is open, however, it is preferred that the tube has a detachable stopper which seals the open end. The stopper can be formed of, for example, a rubber, an elastomer, a resin, or the like. The stopper is freely detachable, but its mechanism is not particularly limited. For example, apart of the stopper may be fixed by being inserted in the inside of a tube portion, or the stopper may be in the form of a cap.

It is preferred that air bubbles or other liquids are not present in the plugs or between plugs, however, air bubbles or other liquids may be present as long as the nucleic acid-binding solid-phase carrier can pass through the plugs.

The plug composed of an oil has a function of preventing the water-soluble plugs disposed on both sides thereof from being mixed with each other.

By using an oil having a higher viscosity as the oil, a "wipe-off effect" of the oil at the interface between the plug composed of the oil and the plug immediately upstream thereof can be enhanced when the nucleic acid-binding solid-phase carrier is moved. Accordingly, when the nucleic acid-binding solid-phase carrier is moved to the plug composed of the oil from the plug immediately upstream thereof, this can make it more difficult to carry over water-soluble components adhered to the nucleic acid-binding solid-phase carrier into the oil.

The length of each of the plugs composed of an oil in the longitudinal direction of the tube is not particularly limited as long as it is within a range capable of forming the plug, however, specifically, it may be 1 mm or more and 50 mm or less, and it is preferably 1 mm or more and 30 mm or less, and more preferably 5 mm or more and 20 mm or less so that the moving distance of the nucleic acid-binding solid-phase carrier is not too long.

The second plug is disposed at a position between the first plug and the third plug in the tube and is composed of a first washing liquid.

The first washing liquid is a liquid immiscible with both the oil constituting the first plug and the oil constituting the third plug. The first washing liquid is not particularly limited as long as it is a solution which does not substantially contain organic solvents such as ethanol and isopropyl alcohol and chaotropic substances, but is preferably water or an aqueous solution with a low salt concentration. In the case of the aqueous solution with a low salt concentration, a buffer is preferred. The salt concentration in the aqueous solution with a low salt concentration is preferably 100 mM or less, more preferably 50 mM or less, and most preferably 15 mM or less. The lower limit of the salt concentration in the aqueous solution with a low salt concentration is not particularly limited, but is preferably 0.1 mM or more, more preferably 1 mM or more, and most preferably 10 mM or more. This solution may contain a surfactant such as Triton, Tween, or SDS, and the pH of the solution is not particularly limited. A salt to be used for forming the buffer is not particularly limited, but a salt such as Tris, HEPES, PIPES, or a phosphate is preferably used.

The volume of the second plug is not particularly limited, and can be suitably set by using the amount of the nucleic acid-binding solid-phase carrier or the like as an index. For example, when the volume of the nucleic acid-binding solid-phase carrier is 0.5 µL, it is sufficient that the volume of the second plug is 10 µL or more, and it is set to preferably 20 µL or more and 50 µL or less, more preferably 20 µL or more and 30 µL, or less. If the volume of the second plug is within this range, in the case where the volume of the nucleic acid-binding solid-phase carrier is 0.5 µL, the nucleic acid-binding solid-phase carrier can be sufficiently washed. The volume of the second plug is preferably larger for washing the nucleic acid-binding solid-phase carrier, but can be suitably set in view of the length and diameter of the tube, the length of the second plug in the longitudinal direction of the tube depending thereon, etc.

The second plug may be constituted by an arbitrary number of plugs by being divided by oil plugs. In the case where the second plug is composed of a plurality of plugs, liquids in the respective plugs may be either the same or different. As long as there is at least one plug composed of the first washing liquid among the plugs, the liquids in the other plugs are not particularly limited, however, it is preferred that all the plugs are composed of the first washing liquid. The number of the divided plugs constituting the second plug can be suitably set in view of, for example, the length of the tube, the object to be washed, etc.

The fourth plug is disposed at a position between the third plug and the fifth plug in the tube and is composed of a reverse transcription reaction solution.

The reverse transcription reaction solution contains a reverse transcriptase, dNTP, and a primer (oligonucleotide) for the reverse transcriptase. A solvent is preferably water, and the reverse transcription reaction solution is preferably a solution which does not substantially contain organic solvents such as ethanol and isopropyl alcohol and chaotropic substances. Further, the reverse transcription reaction solution preferably contains a salt so as to serve as a buffer for the reverse transcriptase. The salt contained in the buffer is not particularly limited as long as it does not inhibit the enzymatic reaction, but a salt such as Tris, HEPES, PIPES, or a phosphate is preferably used. The reverse transcriptase is not particularly limited, and a reverse transcriptase derived from, for example, avian myeloblast virus, Ras associated virus type 2, mouse molony murine leukemia virus, or human immunodefficiency virus type 1, or the like can be used, however, a heat-resistant enzyme is preferred. The concentrations of the dNTP and the salt contained in the reverse transcription reaction solution may be set to concentrations suitable for the reverse transcriptase to be used, however, the concentration of the dNTP may be set to generally 10 to 1000 µM, preferably 100 to 500 µM, the concentration of $Mg^{2+}$ may be set to 1 to 100 mM, preferably 5 to 10 mM, and the concentration of $Cl^-$ may be set to 1 to 2000 mM, preferably 200 to 700 mM. The total ion concentration is not particularly limited, but may be higher than 50 mM, and is preferably higher than 100 mM, more preferably higher than 120 mM, further more preferably higher than 150 mM, and still further more preferably higher than 200 mM. The upper limit thereof is preferably 500 mM or less, more preferably 300 mM or less, and further more preferably 200 mM or less. Each oligonucleotide as the primer is used in an amount of 0.1 to 10 µM, preferably 0.1 to 1 µM. As the carrier, BSA, gelatin, or the like may be contained, however, if the concentration thereof is 1 mg/mL or less, an preventive effect on reaction inhibition is small, and if the concentration thereof is 10 mg/mL or more, it may inhibit the reverse transcription reaction or the subsequent enzymatic reaction, and therefore, the concentration thereof is preferably from 1 to 10 mg/mL. In the case of using gelatin, the gelatin may be derived from, for example, cattle skin, pig skin, or cattle bone, but the origin thereof is not particularly limited thereto. If the gelatin is sparsely soluble, it may be heated to facilitate dissolution.

The volume of the fourth plug is not particularly limited, and can be suitably set by using the amount of the nucleic acid-binding solid-phase carrier having nucleic acids adsorbed thereon or the like as an index. For example, when the volume of the nucleic acid-binding solid-phase carrier is 0.5 µL, it is sufficient that the volume of the fourth plug is 0.5 µL or more, and it is set to preferably 0.8 µL or more and 5 µL or less, more preferably 1 µL or more and 3 µL or less. In the case where the volume of the fourth plug is within these ranges, for example, even if the volume of the nucleic acid-binding solid-phase carrier is set to 0.5 µL, the reverse transcription reaction can be sufficiently performed.

The sixth plug is disposed at a position between the fifth plug and the seventh plug in the tube and is composed of an eluent.

The eluent refers to a liquid which elutes nucleic acids adsorbed on the nucleic acid-binding solid-phase carrier from the carrier in the liquid. The eluent is also not particularly limited, but is preferably water or an aqueous solution with a low salt concentration, and more preferably a solution which does not substantially contain organic solvents such as ethanol and isopropyl alcohol and chaotropic substances. In the case of the aqueous solution with a low salt concentration, a buffer is preferred. The salt concentration in the aqueous solution with a low salt concentration is preferably 100 mM or less, more preferably 50 mM or less, and most preferably 15 mM or less. The lower limit of the salt concentration in the aqueous solution with a low salt concentration is not particularly limited, but is preferably 0.1 mM or more, more preferably 1 mM or more, and most preferably 10 mM or more. A salt to be used for forming the buffer is not particularly limited, but a salt such as Tris, HEPES, PIPES, or a phosphate is preferably used, and TE (10 mM Tris-HCl buffer, 1 mM EDTA, pH 8.0) is most preferred. The first washing liquid and the eluent may be the same or different.

The eluent may further contain a DNA polymerase and a primer (oligonucleotide) for the DNA polymerase, and may also contain a probe for real-time PCR such as a TaqMan probe, a molecular beacon probe, or a cycling probe, or a fluorescent dye for an intercalator such as SYBR green. The DNA polymerase is also not particularly limited, but is preferably a heat-resistant enzyme or an enzyme for use in PCR, and there are a great number of commercially available products such as Taq polymerase, Tfi polymerase, Tth polymerase, and a modified form thereof. Further, the eluent preferably contains BSA (bovine serum albumin) or gelatin as a preventive agent for reaction inhibition.

The concentrations of the dNTP and the salt contained in the eluent may be set to concentrations suitable for the DNA polymerase to be used, however, the concentration of the dNTP may be set to generally 10 to 1000 µM, preferably 100 to 500 µM, the concentration of $Mg^{2+}$ may be set to 1 to 100 mM, preferably 5 to 10 mM, and the concentration of $Cl^-$ may be set to 1 to 2000 mM, preferably 200 to 700 mM. The total ion concentration is not particularly limited, but may be higher than 50 mM, and is preferably higher than 100 mM, more preferably higher than 120 mM, further more preferably higher than 150 mM, and still further more preferably higher than 200 mM. The upper limit thereof is preferably 500 mM or less, more preferably 300 mM or less, and further more preferably 200 mM or less. Each oligonucleotide as the primer is used in an amount of 0.1 to 10 µM, and preferably 0.1 to 1 µM. As the carrier, BSA, gelatin, or the like may be contained, however, if the concentration thereof is 1 mg/mL or less, a preventive effect on reaction inhibition is small, and if the concentration thereof is 10 mg/mL or more, it may inhibit the polymerization reaction or the subsequent enzymatic reaction, and therefore, the concentration thereof is preferably from 1 to 10 mg/mL. In the case of using gelatin, the gelatin may be derived from, for example, cattle skin, pig skin, or cattle bone, but the origin thereof is not particularly limited thereto. If the gelatin is sparsely soluble, it may be heated to facilitate dissolution.

The volume of the sixth plug is not particularly limited, and can be suitably set by using the amount of the nucleic acid-binding solid-phase carrier having nucleic acids adsorbed thereon or the like as an index. For example, when the volume of the nucleic acid-binding solid-phase carrier is 0.5 µL, it is sufficient that the volume of the sixth plug is 0.5 µL or more, and it is set to preferably 0.8 µL or more and 5 µL or less, more preferably 1 µL or more and 3 µL or less. In the case where the volume of the sixth plug is within these ranges, for example, even if the volume of the nucleic acid-binding solid-phase carrier is set to 0.5 µL, the reverse transcription reaction can be sufficiently performed.

In the case where the eluent contains a DNA polymerase and a primer for the DNA polymerase, the eluent after elution can be used directly in a DNA polymerase reaction. At this time, the reaction may be performed in the tube, however, the eluent is discharged outside the tube and newly transferred to a container for a DNA polymerase reaction, and the reaction may be performed. In the case where the DNA polymerase reaction is performed outside the tube, a part or the whole of the eluent may be used. In the case where a part of the eluent is used, it is preferably diluted with a buffer adjusted for the DNA polymerase. As the buffer adjusted for the DNA polymerase, a solution containing the same components as the eluent may be used, however, it is preferred that the salt concentration in the buffer is suitably adjusted, and it does not matter whether or not a DNA polymerase, dNTP, and a primer for the DNA polymerase are added thereto.

This nucleic acid extraction device may be further provided with a plug at an arbitrary place as desired other than the first to seventh plugs. In consideration that a plug composed of an oil prevents water-soluble plugs disposed on both sides thereof from mixing with each other, it is preferred that a plug composed of an oil and a water-soluble plug are alternately disposed, and in the case where a water-soluble plug is added, a plug composed of an oil may be disposed between the adjacent water-soluble plugs.

For example, between the third plug and the fourth plug, in order from the third plug side, an eighth plug composed of a second washing liquid immiscible with an oil and a ninth plug composed of an oil may be disposed. In this case, the second washing liquid is a liquid immiscible with both the oil constituting the third plug and the oil constituting the ninth plug. The second washing liquid may have a composition which is the same as or different from that of the first washing liquid. However, the way of selection of the basic structure of the eighth plug conforms to that of the second plug.

When a plurality of plugs composed of a washing liquid are provided upstream of the plug composed of a reverse transcription reaction solution in this manner, a chaotropic agent may be incorporated in the washing liquid on the upstream side. For example, when guanidine hydrochloride is incorporated in the first washing liquid of the second plug, it is possible to wash nucleic acids adsorbed on the nucleic acid-binding solid-phase carrier in the second plug while maintaining or enhancing the adsorption of the nucleic acids adsorbed on the nucleic acid-binding solid-phase carrier. The concentration of guanidine hydrochloride in the case where guanidine hydrochloride is incorporated in the second plug can be set to, for example, 3 mol/L or more and 10 mol/L or less, preferably 5 mol/L or more and 8 mol/L or less. If the concentration of guanidine hydrochloride is within this range, while more stably adsorbing nucleic acids adsorbed on the nucleic acid-binding solid-phase carrier, the other foreign substances and the like can be washed off. Then, by using water or a buffer as the second washing liquid of the eighth plug, washing can be performed while more stably adsorbing nucleic acids adsorbed on the nucleic acid-binding solid-phase carrier in the second plug, and also in the eighth plug, the carrier can be further washed while removing the chaotropic agent.

Further, between the fifth plug and the sixth plug, in order from the fifth plug side, a tenth plug composed of a third washing liquid immiscible with an oil and an eleventh plug composed of an oil may be disposed. Also in this case, the third washing liquid is a liquid immiscible with both the oil constituting the fifth plug and the oil constituting the eleventh plug. The third washing liquid may have a composition which is the same as or different from that of the first washing liquid. However, the way of selection of the basic structure of the tenth plug conforms to that of the second plug.

In the case where a plug composed of a washing liquid is provided downstream of the plug composed of a reverse transcription reaction solution in this manner, in particular, in the case where a DNA polymerase reaction is performed in the seventh plug, the carry-over of the reverse transcription reaction solution into the DNA polymerase reaction solution is reduced, and thus, an effect of increasing the efficiency of the DNA polymerase reaction is exhibited.

Nucleic Acid Extraction Apparatus

The nucleic acid extraction apparatus according to the embodiment of the invention includes the above-described nucleic acid extraction device and a magnetic force application device which applies a magnetic force and is provided for a tube, and if desired also for a tank. In the case where the nucleic acid extraction apparatus includes a plurality of tubes, the magnetic force application device is preferably configured such that it can simultaneously apply a magnetic force to corresponding portions of the tubes. The magnetic force application device is not particularly limited, and examples thereof include permanent magnets and electromagnets. From the viewpoint that heat is not generated and so on, permanent magnets are more preferred. When nucleic acids are extracted, it is desired to move the magnetic force application device, and thus, a magnetic force application device moving unit that automatically moves the magnetic force application device may be provided. Alternatively, the nucleic acid extraction device may be moved with respect to the magnetic force application device, and in this case, a nucleic acid extraction device moving unit may be provided.

The nucleic acid extraction apparatus according to the embodiment of the invention may further include a heating unit which is disposed at a position where the unit heats the fourth plug composed of a reverse transcription reaction solution and the sixth plug composed of an eluent of the tube. Here, a heating unit which controls the fourth plug and the sixth plug may be provided, however, a plurality of heating units which separately control the respective plugs may be provided. The heating unit is not particularly limited, but for example, a heat block, a heater, an electromagnetic heater or the like can be used.

Further, a nucleic acid extraction kit may be formed such that it includes a lysis solution for lysing a sample from which nucleic acids are extracted, a nucleic acid-binding solid-phase carrier having a magnetic material, and the nucleic acid extraction device. According to this, a kit can be formed such that it includes only disposable members among the members to be used in this nucleic acid extraction apparatus.

Nucleic Acid Extraction Method

The above-described nucleic acid extraction apparatus can be preferably used for the nucleic acid extraction method according to an embodiment of the invention. A sample from which nucleic acids are extracted is not particularly limited as long as it contains nucleic acids, and may be a biological sample such as cells or cell clusters (such as tissues), viruses, synthetic nucleic acids, a sample in which impurities or foreign substances are mixed with once isolated nucleic acids, or the like.

First, the above-described nucleic acid extraction device is attached to a fixing unit such that the longitudinal direction of a single tube or a plurality of tubes is parallel with the gravitational direction.

Subsequently, a nucleic acid-binding solid-phase carrier having a magnetic material, a lysis solution, and a sample from which nucleic acids are extracted are fed to a tank. The order in which these materials are fed is not limited. A specific method may include, for example, the following steps, however, in this case, the order in which the respective steps are performed is not particularly limited: (1) a step of feeding a sample to a lysis solution and mixing the sample with the lysis solution; (2) a step of adding a nucleic acid-binding solid-phase carrier having a magnetic material to a lysis solution; (3) a step of feeding the lysis solution mixed with the sample to a tank of the nucleic acid extraction device; and (4) a step of homogenizing the nucleic acid-binding solid-phase carrier having nucleic acids bound thereto in the lysis solution.

For example, the following procedure may be adopted. A sample from which nucleic acids are extracted and a nucleic acid-binding solid-phase carrier are fed to a lysis solution for lysing the sample and mixed therewith (1) (2), the sample is lysed using a homogenizer or a vortex mixer (4), and thereafter the thus obtained homogenate is fed to a tank (3). Alternatively, a sample is lysed alone (1), the lysed sample and a nucleic acid-binding solid-phase carrier are separately fed to a tank (2) (3), and then, the opening of a nucleic acid extraction device is capped and the sample and the carrier are well mixed with each other (4). Alternatively, a sample is lysed alone (1), the lysed sample and a nucleic acid-binding solid-phase carrier are mixed (2), and then mixed well (4), and then, the resulting mixture is fed to a tank (3). By this procedure, nucleic acids in the sample are adsorbed on the nucleic acid-binding solid-phase carrier.

If a nucleic acid-binding solid-phase carrier having a magnetic material and/or a lysis solution have/has already been placed in a tank, it is only necessary to feed a sample from which nucleic acids are extracted to the tank, and if the carrier or the lysis solution is lacking, it is only necessary to feed the lacking component along with the sample to the tank.

In the case where a plurality of tubes are provided, since the nucleic acid extraction device is attached to the fixing unit such that the longitudinal direction of the tubes is parallel with the gravitational direction, the carrier is uniformly introduced into all the tubes. In the case where a partition wall for separating spaces communicating to the respective tubes is provided in the tank, by raising the liquid level of the lysis solution containing the sample lysate and the carrier above the partition wall, the carrier is uniformly introduced into the respective tubes.

Thereafter, since the nucleic acid-binding solid-phase carrier has a magnetic material, by using a magnetic force application device capable of simultaneously applying a magnetic force to corresponding portions of the single tube or plurality of tubes, a magnetic force is applied in the direction from the first plug to the sixth plug, whereby the nucleic acid-binding solid-phase carrier can be moved from the inside of the tank to the sixth plug. At this time, in the case where a permanent magnet is used, this procedure may be performed by moving the magnet with the hand of an operator, or by utilizing a magnetic force application device moving unit or the like. A retention time in each plug when the nucleic acid-binding solid-phase carrier passes through the respective plugs is not particularly limited. The magnetic force application device may be moved reciprocatively along the longitudinal direction of the tube in the same plug. Further, the magnetic force application device may be oscillated in the direction at an angle with respect to the moving direction (for example, substantially perpendicularly). This oscillation can be applied to any of the plugs, however, for example, by applying such oscillation to the second plug composed of a washing liquid, a washing effect can be enhanced.

When the nucleic acid-binding solid-phase carrier washed in the second plug is moved to the fourth plug, a reverse transcription reaction is performed there. The reaction may be performed under the conditions suitable for a reverse transcriptase to be used. For example, the reverse transcription reaction solution is heated to 30 to 50° C., preferably 42 to 45° C., and the nucleic acid-binding solid-phase carrier is maintained therein for a given time, whereby the reverse transcription reaction can be carried out while binding RNA to the carrier. The heating method is not particularly limited, however, for example, a method in which a heat medium such as a heat block is brought into contact with a portion corresponding to the fourth plug of the tube, a method in which a heat source such as a heater is used, a method in which electromagnetic heating is performed, or the like can be used. Also, the retention time can be suitably selected by an operator, but may be set to 10 seconds to 5 minutes, preferably 30 seconds to 1 minute. cDNA synthesized at this stage is bound to the solid phase carrier in a state of being bound to the RNA.

Thereafter, the nucleic acid-binding solid-phase carrier is moved in the eluent of the sixth plug. Here, in order to efficiently release the nucleic acids, particularly cDNA from the nucleic acid-binding solid-phase carrier, it is preferred to heat the sixth plug. The heating method is not particularly limited, but the same method as used for heating the fourth plug can be used. The heating temperature may be higher than 40° C., and is preferably 50° C. or higher, and more preferably 60° C. or higher. The upper limit of the heating temperature is not particularly limited, but is preferably 70° C. or lower, more preferably 65° C. or lower, further more preferably 60° C. or lower, and most preferably 60° C.

After the nucleic acids are released from the nucleic acid-binding solid-phase carrier, by using the magnetic force application device, the nucleic acid-binding solid-phase carrier is moved from the sixth plug to the upper side. It does not matter where the nucleic acid-binding solid-phase carrier is moved as long as it is not mixed in the eluent of the sixth plug.

Thereafter, the nucleic acids released in the eluent of the sixth plug are recovered. For example, in the case where a flexible material such as a rubber, an elastomer, or a polymer is used as a material for the tank, when pressure is applied to the inside of the tank by detaching the stopper at the end of the tube and deforming the tank in a state where the cap is attached to the tank, the solution in the tube is discharged from the end of the tube. First, the oil of the seventh plug is discharged, and thereafter, the eluent of the sixth plug is discharged.

The cDNA eluted in this manner can be directly used in an enzymatic reaction such as PCR without performing a desalting or concentration procedure such as dialysis or ethanol precipitation. The cDNA may be isolated from the eluent, and for example, in order to remove RNA, an RNase may be added to the obtained eluent, however, an RNase may be incorporated in advance in the eluent. For example, by incorporating ribonuclease A in the eluent in an amount of 10 to 20 µg/mL, RNA can be efficiently degraded. In general, a procedure such as PCR can be performed while incorporating an RNase, however, when the RNase is desired to be removed, by repeating the method according to the embodiment of the invention again or by another known method, the cDNA may be purified.

It is also possible to incorporate a DNA polymerase, dNTP, and a primer (oligonucleotide) for the DNA polymerase in advance in the eluent. According to this, by using the solution recovered from the sixth plug as such, PCR can be performed directly.

Incidentally, PCR may be performed in the sixth plug while retaining the nucleic acids in the tube without recovering the nucleic acids released in the eluent of the sixth plug. In this case, it is desired to incorporate a PCR enzyme, dNTP, and a primer (oligonucleotide) for the PCR enzyme in advance in the eluent. The heating method for the PCR is not particularly limited, however, the same method as used for heating the fourth plug may be used, and also a thermal cycling PCR method may be used. After the PCR, the amplified cDNA may be recovered. The recovery method is not particularly limited, and the same method as in the case where cDNA is recovered without being amplified can be used.

EXAMPLES (1) Structure of Nucleic Acid Extraction Device I

Figure 1B:
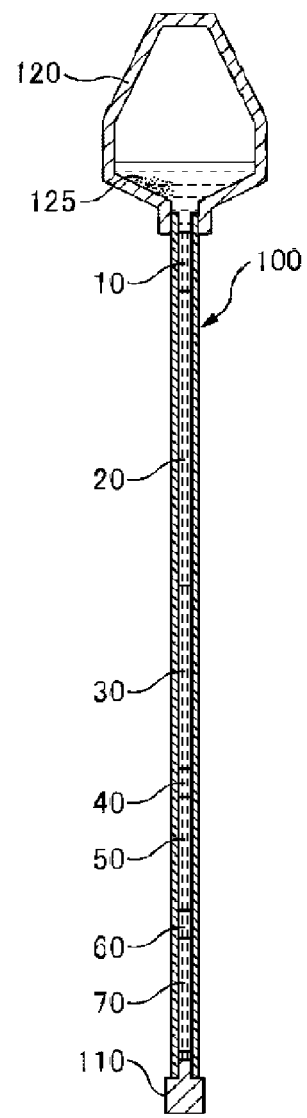

FIG. 1A shows an exploded view of a nucleic acid extraction device before assembly, and FIG. 1B shows a completed view of the device after assembly.

This device includes one capillary 100 (i.e., a tube) and a tank 120 for injecting a liquid into the capillary 100. The capillary 100 and the tank 120 can constitute a kit 130 for assembling a nucleic acid extraction device.

The capillary 100 has a stopper 110, and is internally provided with first to seventh plugs which are composed of an oil 10, a washing liquid 20, an oil 30, a reverse transcription reaction solution 40, an oil 50, an eluent 60, and an oil 70 in this order, respectively. The oils separate the respective aqueous solutions.

The tank 120 has an opening 121, a detachable cap 122 for the opening 121, a space 123, and a lysis solution 124. In the lysis solution 124, magnetic beads 125 in which nucleic acids are adsorbed on surface-coated silica are contained.

The capillary 100 and the tank 120 can be connected to each other as shown in FIG. 1B by removing the stopper 110 and the cap 122, respectively.

(2) Structure of Nucleic Acid Extraction Device II

Figure 2:
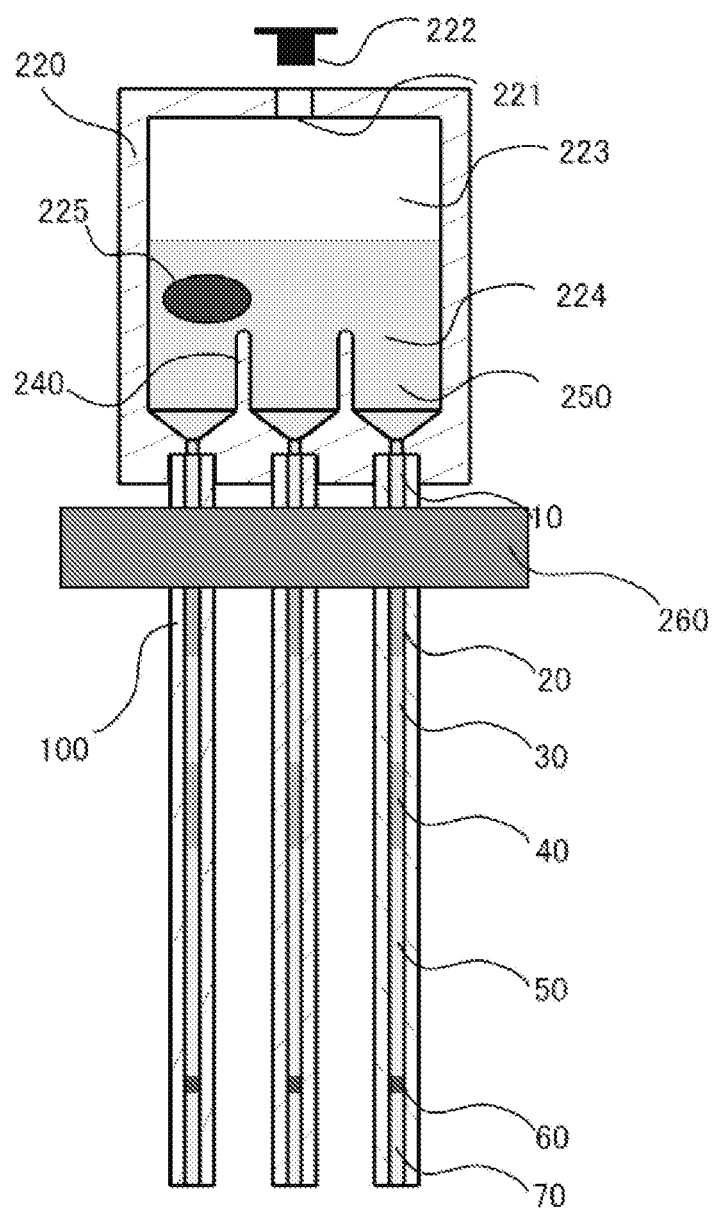
FIG. 2 is a schematic view showing a structure of a nucleic acid extraction device according to an embodiment of the invention.

A device shown in FIG. 2 has a plurality of capillaries 100 (i.e., tubes), a tank 220 for injecting a liquid into the capillaries 100, and rectangular magnets 260.

The tank 220 has an opening 221, a detachable cap 222 for the opening 221, a space 223, a lysis solution 224, partition walls 240 in a liquid dispensing section, and compartments 250 surrounded by the inner walls of the tank 220 and the partition walls 240. In the lysis solution 224, magnetic beads 225 in which nucleic acids are adsorbed on surface-coated silica are contained.

The plurality of capillaries 100 are provided such that they are independently linearly arranged in parallel with each other. By linearly arranging the capillaries 100, the rectangular magnets 260 facing each other can easily sandwich the plurality of capillaries 100 therebetween and can simultaneously apply a magnetic force to corresponding portions of the plurality of capillaries 100 by a simple operation such as an up-and-down movement. According to this, it becomes easy to allow the magnetic beads 225 to perform the same movement in the plurality of capillaries 100, and an automated apparatus can be simplified. Each capillary 100 is internally provided with first to seventh plugs which are composed of an oil 10, a washing liquid 20, an oil 30, a reverse transcription reaction solution 40, an oil 50, an eluent 60, and an oil 70 in this order, respectively.

(3) Structure of Nucleic Acid Extraction Apparatus

Figure 3:
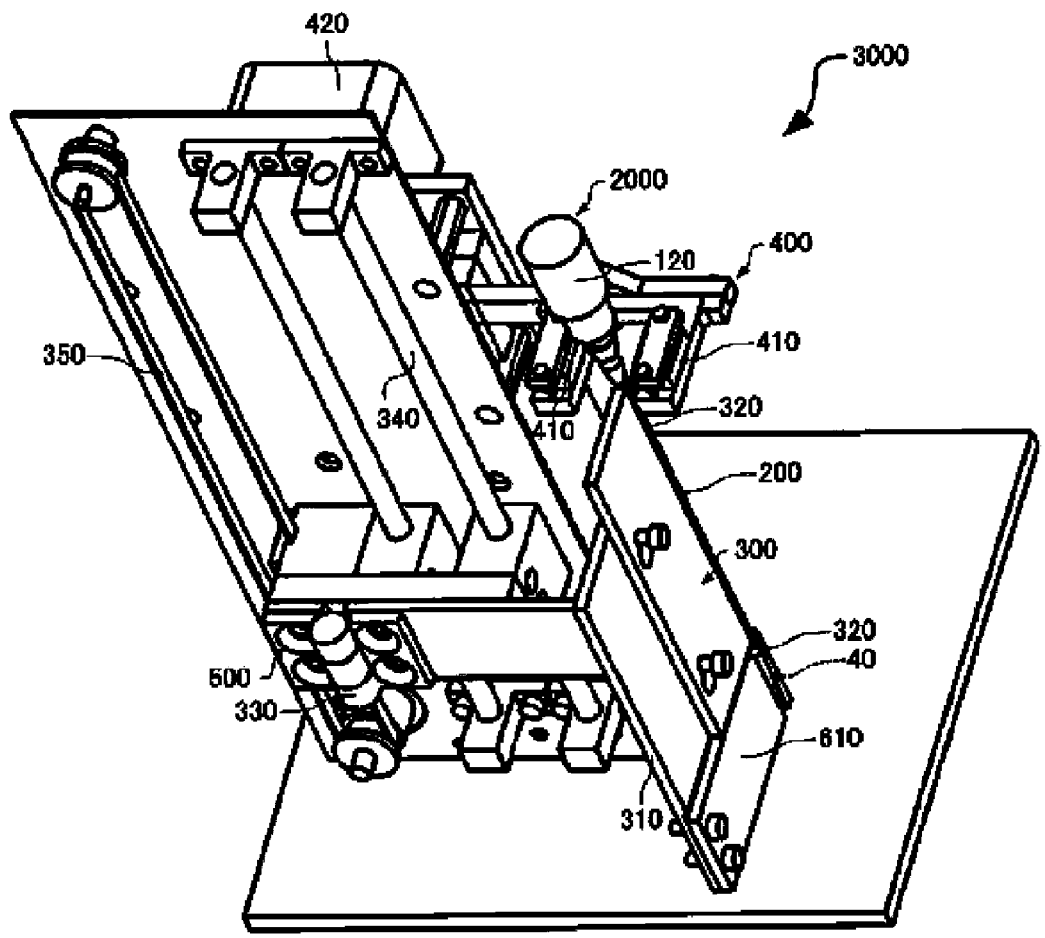
FIG. 3 is a schematic view showing a structure of a nucleic acid extraction apparatus according to an embodiment of the invention.

A nucleic acid extraction apparatus 3000 according to an embodiment of the invention is an apparatus which is mounted with the nucleic acid extraction device 2000 of (1) and extracts nucleic acids (FIG. 3). This apparatus 3000 includes a mounting section 300 for mounting the nucleic acid extraction device 2000 while being supported by a capillary 200 (i.e., tube), a magnetic force application section 400 for applying a magnetic force to the capillary 200 and if desired to a tank 120 from a side surface thereof when the nucleic acid extraction device 2000 is mounted on the mounting section 300, a moving mechanism 500 for changing a relative position between the mounting section 300 and the magnetic force application section 400 along the longitudinal direction of the capillary 200, and a heating section 600 for heating a part of the capillary 200. By changing the relative positional relationship between the mounting section 300 and the magnetic force application section 400, magnetic particles in the nucleic acid extraction device 2000 can be moved therein.

The mounting section 300 has a supporting plate 310 so that the capillary 200 is disposed along the plate. By this supporting plate 310, the capillary 200 can be prevented from oscillating or the like. The mounting section 300 further has clip mechanisms 320, with which the capillary 200 is fixed at two sites.

The mounting section 300 is configured such that the positional relationship with the magnetic force application section 400 can be relatively changed with respect to the longitudinal direction of the capillary 200. In this Example, since the apparatus is designed such that the mounting section 300 is relatively moved with respect to the magnetic force application section 400 without moving the magnetic force application section 400, the moving mechanism 500 which moves the mounting section 300 is provided. The mounting section 300 is provided with a hinge 330, a guide rail 340, a driving belt 350, and a motor 420.

The magnetic force application section 400 is provided with a pair of rectangular magnets 410 facing each other and sandwiching the tank 120 and the capillary 200 therebetween. The pair of rectangular magnets 410 are disposed apart at a distance larger than the outer diameter of the capillary 200. The magnetic force application section 400 is disposed such that when one of the pair of rectangular magnets 410 moves closer to the capillary 200, the other rectangular magnet 410 moves away from the capillary 200, and the pair of rectangular magnets 410 can be oscillated by the motor 420 so that the magnets move closer to or away from the capillary 200 (a detailed description will be given later). The motor 420 can perform driving as desired wherever a magnetic force is applied to the tank 120 or the capillary 200.

The heating section 600 is provided with two heaters which are independently controlled and can heat the fourth plug and the sixth plug of the capillary 200 when the capillary 200 is mounted on the mounting section 300.

The nucleic acid extraction apparatus 3000 can elute a sufficient amount of nucleic acids with the eluent of the fourth plug 40 by washing with at least one of the first washing liquid of the second plug 20 and the second washing liquid of the sixth plug 60 even if the amount of nucleic acids adsorbed on the magnetic particles M is decreased. Accordingly, the washing effect can be enhanced and also a sufficient concentration of nucleic acids for PCR can be eluted with the eluent.

(4) How to Use Rectangular Magnets

Figure 4:
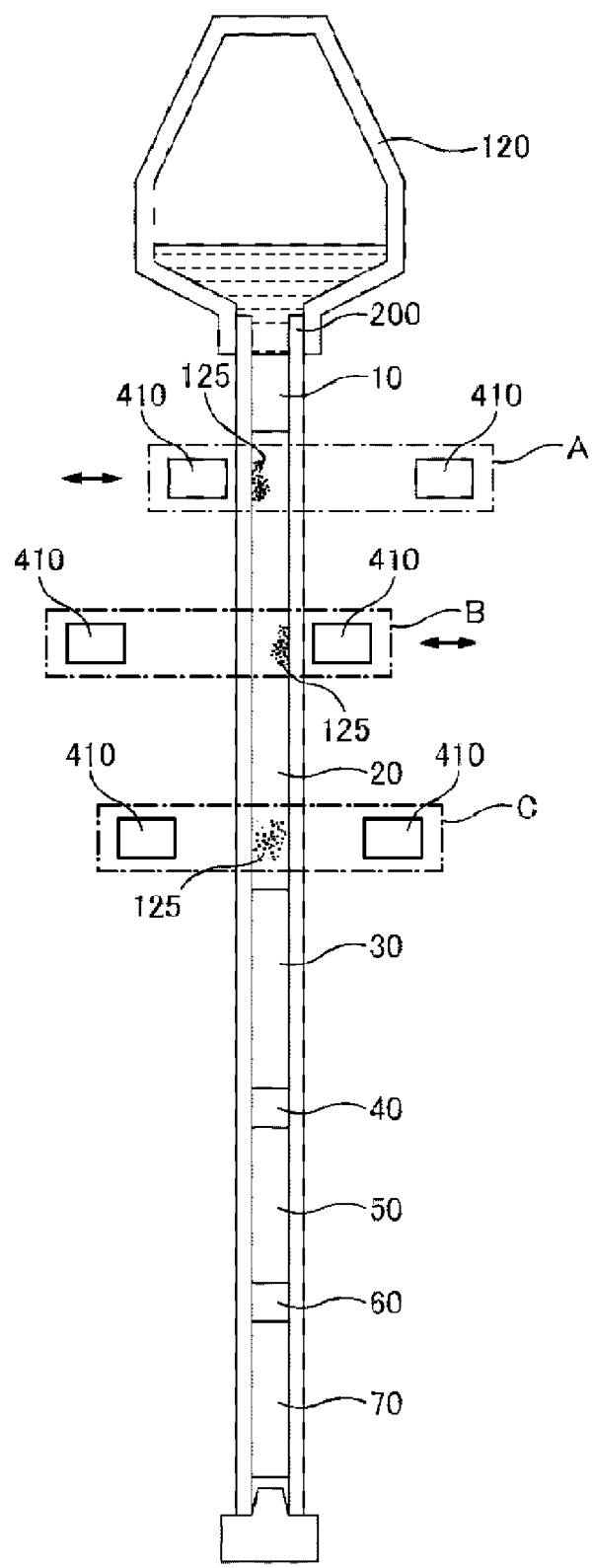
FIG. 4 is a view showing how to use rectangular magnets in a nucleic acid extraction method according to an embodiment of the invention.

FIG. 4 shows the capillary 200 and the rectangular magnets 410 in the nucleic acid extraction apparatus and how to use the rectangular magnets 410.

The rectangular magnets 410 facing each other easily sandwich the capillary 200 and apply a magnetic force to the capillary 200 by a simple operation such as an up-and-down movement, and thus, the magnetic beads 125 in the capillary 200 can be moved up and down. According to this, an automated apparatus can be simplified.

Further, for example, as shown in the dashed line rectangle indicated by the letter A, by bringing the rectangular magnet 410 on the left side of the rectangular magnets 410 provided on both sides closer to the capillary 200, the magnetic beads 125 are gathered on the left side of the capillary 200, and as shown in the dashed line rectangle indicated by the letter B, by bringing the rectangular magnet 410 on the right side closer to the capillary 200, the magnetic beads 125 are gathered on the right side of the capillary 200. Further, as shown in the dashed line rectangle indicated by the letter C, by separating both the rectangular magnets 410 from the capillary 200, the magnetic beads 125 are dispersed in the capillary 200. Accordingly, by moving the rectangular magnets 410 right and left at the same place, a state indicated by the letter A and a state indicated by the letter B can be repeated, and thus, the magnetic beads 125 can be oscillated.

(5) Nucleic Acid Extraction Method

Hereinafter, a nucleic acid extraction method using the nucleic acid extraction apparatus 3000 having one capillary 200 will be described.

In the diagnosis of influenza, after the cap 122 of the tank 130 is detached, a specimen collected from the mucosa in the throat with a cotton swab is inserted into the tank 130 containing the lysis solution 124 to soak the cotton swab used for collecting the specimen in the lysis solution 124, whereby a virus is collected in the lysis solution 124. In the lysis solution 124, the magnetic beads 125 surface-coated with silica are contained. By closing the tank 130 with the cap 122 and shaking the tank 130, nucleic acids are adsorbed on the magnetic beads 125.

Subsequently, the cap 122 of the tank 130 is detached again, the upper stopper 110 of the capillary 100 is detached, and the tank 130 and the capillary 100 are connected to each other. Then, the capillary is disposed in parallel with the gravitational direction.

Thereafter, by moving the magnetic beads 125 in the gravitational direction along the capillary 100 using the rectangular magnets 410, the magnetic beads 125 are allowed to pass through the respective plugs. Along the way, as shown in FIG. 4, by alternately using the rectangular magnets 410 disposed right and left, the magnetic beads 125 may be oscillated right and left.

The magnetic beads 125 are moved to the fourth plug previously heated to 45° C. by the heat block, and then brought to a standstill for 30 seconds to effect a reverse transcription reaction.

Thereafter, the magnetic beads 125 are further moved to the sixth plug previously heated to 80° C. by the heat block, and cDNA on the magnetic beads is eluted by oscillating the rectangular magnets 410 for 30 seconds.

Finally, the lower stopper 110 of the capillary 100 is detached, and the tank 120 is compressed by pushing the tank 120 on both sides by fingers to apply pressure to the inside of the tank 120, whereby the oil 70 and the eluent 60 are ejected from the lower end of the capillary 100, and thus, the eluent 60 containing the eluted cDNA can be collected in another container.

Alternatively, PCR may be performed in the sixth plug.

(6) Comparison between One-Step Elution and Two-Step Elution

By using a capillary having an inner diameter of 1.0 mm and a length of 100 mm and a tank having a volume of 10 mL, a nucleic acid extraction device (for two-step elution) having first to seventh plugs was produced. Here, the volume of the second plug was set to 25 µL, and the volumes of the fourth and sixth plugs were both set to 2 µL. Further, the length of each oil plug was set to 12.5 mm. As the solutions of the respective plugs, the following solutions were used.

Second plug: 5 mM Tris-HCl buffer

Fourth plug:

0.2 u/µL AMV reverse transcriptase (Nippon Gene Co., Ltd.)

0.8 mM dNTP
0.5 μM primer (reverse)
2.0 mg/mL BSA
×1 buffer (7 mM MgCl$_2$, 25 mM Tris pH 9.0, 50 mM KCl)
Sixth plug:
0.05 u/μL Gene Taq NT PCR enzyme (Nippon Gene Co., Ltd.)
0.5 mM dNTP
0.5 μM primer (forward)
0.5 μM primer (reverse)
0.25 μM probe (Taq man)
2.0 mg/mL BSA
×1 buffer (7 mM MgCl$_2$, 25 mM Tris pH 9.0, 50 mM KCl)

As a control, a capillary (for one-step elution) in which the sixth and seventh plugs were not included and the following solution obtained by mixing a PCR reagent was contained in the fourth plug was used.

Fourth plug:
0.2 u/μL AMV reverse transcriptase (Nippon Gene Co., Ltd.)
0.125 u/μL Gene Taq NT PCR enzyme (Nippon Gene Co., Ltd.)
0.5 mM dNTP
1.0 μM primer (forward)
1.0 μM primer (reverse)
0.5 μM probe (Taq man)
4.0 mg/mL BSA
×1 buffer (7 mM MgCl$_2$, 25 mM Tris pH 9.0, 50 mM KCl)
Oligonucleotide sequence:

```
Primer (forward):
                                        (SEQ ID NO 1)
GAC CAA TCC TGT CAC CTC TGA C Primer (reverse):
                                        (SEQ ID NO 2)
AGG GCA TTT TGG ACA AAG CGT CTA Probe (Taq man):
                                        (SEQ ID NO 3)
FAM-TGC AGT CCT CGC TCA CTG GGC ACG-TAMRA
```

With respect to these capillaries, the following three types of capillaries: one immediately after being produced; one stored at 4° C. for 1 week; and one stored at 4° C. for 6 months were used in the following experiment.

In the tank, 350 μL of a lysis solution [5 M guanidine thiocyanate, 2% Triton X-100, 50 mM Tris-HCl (pH 7.2)] and 2 μL of a dispersion of magnetic beads were placed. A cotton swab used for collecting a specimen was soaked therein, and the tank was capped and shaken about 100 times for 30 seconds to effect mixing. As the dispersion of magnetic beads, an aqueous solution of 30 mass % sodium chloride containing 30 vol % magnetic silica particles (NPK-401, Toyobo Co., Ltd.) was used.

Figure 5A:
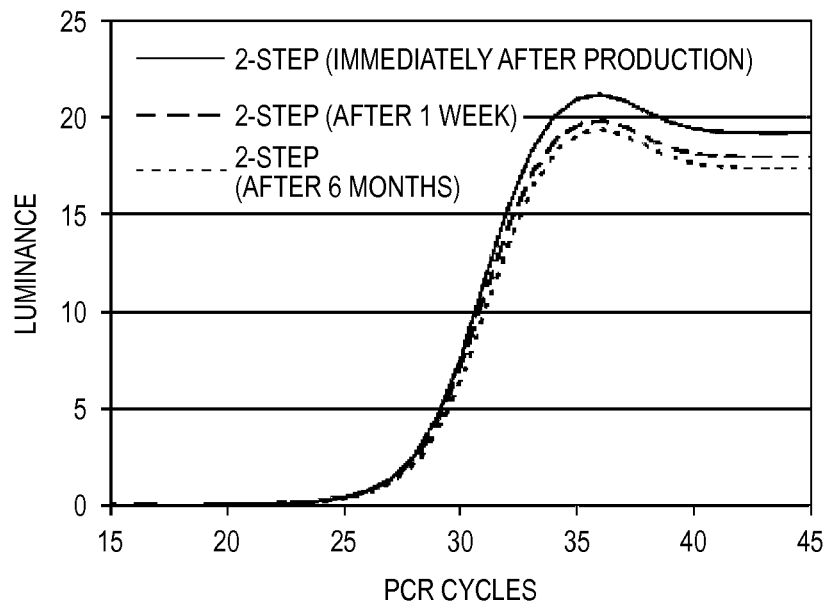
FIGS. 5A and 5B are graphs showing a comparison of changes in detection sensitivity over time when performing PCR using nucleic acid-containing eluents obtained using a capillary for one-step elution (1-step) and a capillary for two-step elution (2-step), respectively, in an embodiment of the invention.
Figure 5B:
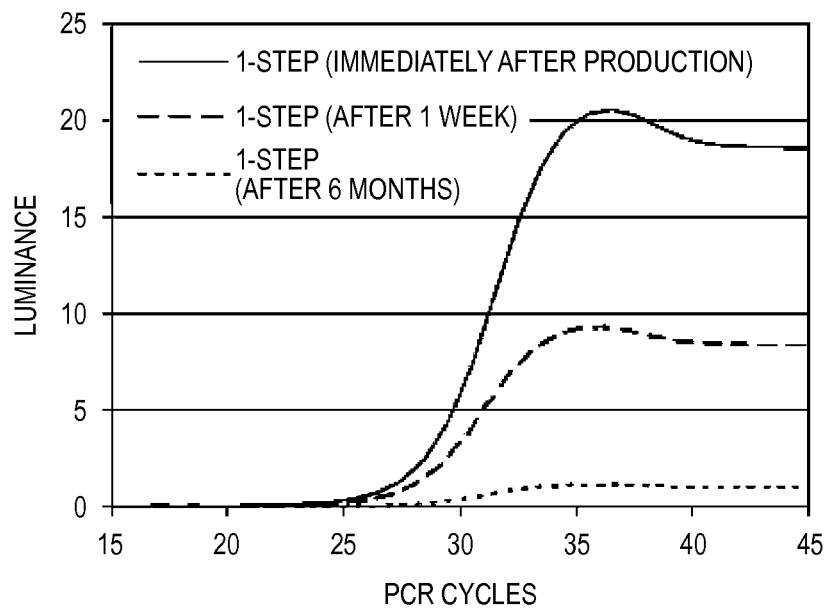

The thus prepared tank was connected to the capillary, and the nucleic acid extraction device was disposed such that the longitudinal direction of the capillary is parallel with the gravitational direction. Then, a magnet was brought into contact with the side surface of the container, and according to the above-described method, the steps of washing, reverse transcription, and elution were performed, and the eluent was discharged outside the capillary. The entire amount (2 μL) of the obtained eluent was subjected to PCR by using a thermal cycling PCR apparatus (an apparatus described in Example 1 in the specification of Japanese Patent Application No. 2010-268090). FIGS. 5A and 5B show a change in luminance with the progression of PCR cycles.

FIGS. 5A and 5B reveal that in the case of the one-step elution of the control, the detection sensitivity decreased already in a week after the production of the capillary, and almost no luminance could be detected after 6 months passed, on the other hand, in the case of the two-step elution in the embodiment of the invention, even after 6 months passed from the date of the production of the capillary, a decrease in detection sensitivity was almost not observed.

Figure 6:
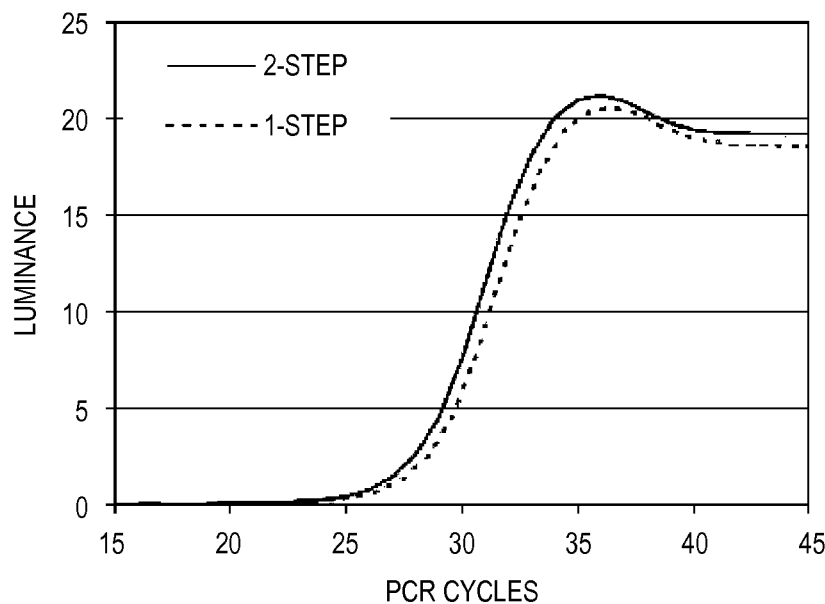
FIG. 6 is a graph showing a comparison of detection sensitivity when performing PCR using nucleic acid-containing eluents obtained using a capillary for one-step elution (1-step) and a capillary for two-step elution (2-step), respectively, in an embodiment of the invention.

Even when a comparison was made immediately after the production of capillary (FIG. 6), the detection sensitivity was higher in the case of the two-step elution in the embodiment of the invention than in the case of the one-step elution of the control.

(7) When Increasing Washing Plug

Figure 7:
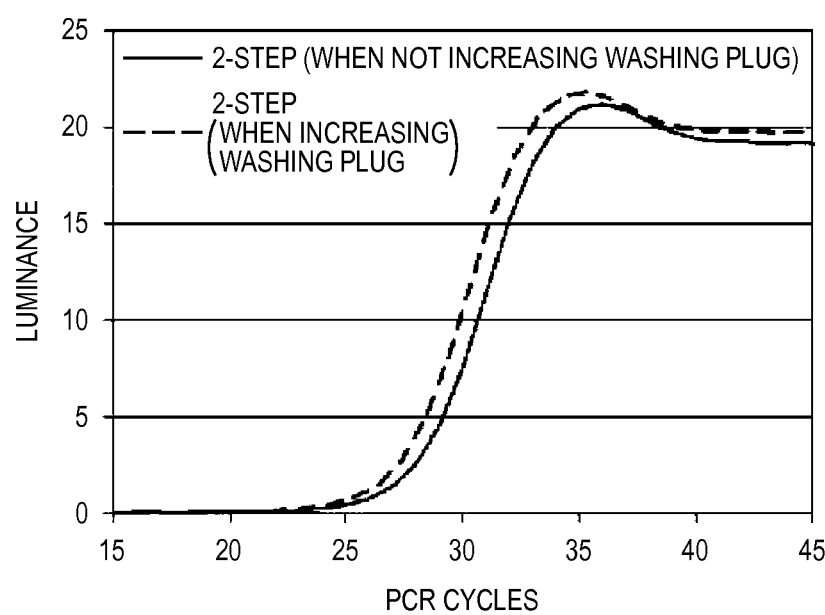
FIG. 7 is a graph showing a comparison of detection sensitivity when performing PCR using nucleic acid-containing eluents obtained using a capillary for two-step elution (2-step) of an embodiment of the invention in the case where a plug composed of a washing liquid was additionally provided downstream of a plug composed of a reverse transcription reaction solution and the case where the plug composed of a washing liquid was not additionally provided.

A capillary which was provided with, between the fifth plug and the sixth plug in order from the fifth plug side, a tenth plug composed of a washing liquid immiscible with an oil and an eleventh plug composed of an oil was produced, and an experiment was performed immediately after the production. As the tenth plug, a plug which was the same as the second plug was used, and as the eleventh plug, a plug which was the same as the other oil plugs was used. The experiment was performed in the same manner as in (6) except for the capillary. FIG. 7 shows a change in luminance with the progression of PCR cycles.

The results were compared with the case where the washing plug was not increased in the same manner as in (6) (FIG. 7), and it was found that the amplification efficiency by PCR was higher in the case where the washing plug was increased.

The entire disclosures of Japanese Patent Application Nos. 2012-237068 filed Oct. 26, 2012 and 2012-237069 filed Oct. 26, 2012 are expressly incorporated by reference herein.

What is claimed is:

1. A nucleic acid extraction device, comprising a tube that is internally provided with, in the following order from a first end of the tube to a second end of the tube:
a first plug composed of a first oil,
a second plug composed of a first washing liquid, which is phase-separated from an oil and is configured to wash a nucleic acid-binding solid-phase carrier having nucleic acids bound thereto,
a third plug composed of a second oil,
a fourth plug composed of a reverse transcription reaction solution, which is phase-separated from an oil and is configured to perform a reverse transcription reaction,
a fifth plug composed of a third oil,
a sixth plug composed of an eluent, which is phase-separated from an oil and is configured to elute the nucleic acids from the nucleic acid-binding solid-phase carrier having nucleic acids bound thereto, and
a seventh plug composed of a fourth oil,
wherein the device is configured such that the nucleic acid-binding carrier can move from the first plug, through the second, third, fourth, and fifth plugs, and to the sixth plug.

2. The nucleic acid extraction device according to claim 1, wherein the tube is provided with, between the fifth plug and the sixth plug in order from the fifth plug side,
a plug composed of a second washing liquid, which is phase-separated from an oil and is configured to wash the nucleic acid-binding solid-phase carrier having nucleic acids bound thereto, and
another plug composed of an oil.

3. The nucleic acid extraction device according to claim 1, wherein the eluent contains a DNA polymerase, dNTP, and a primer for the DNA polymerase.

4. The nucleic acid extraction device according to claim 1, wherein the second end of the tube is an open end which is open, and the tube has a detachable stopper which seals the open end.

5. The nucleic acid extraction device according to claim 1, further comprising a tank connectable to the tube and introduces the nucleic acid-binding solid-phase carrier into the tube.

6. The nucleic acid extraction device according to claim 5, wherein the tank and the tube are detachable from each other.

7. The nucleic acid extraction device according to claim 5, wherein the tank contains a lysis solution for lysing a sample from which nucleic acids are extracted.

8. A nucleic acid extraction method, comprising:
disposing the nucleic acid extraction device according to claim 7 such that a longitudinal direction of the tube is parallel with a gravitational direction;
feeding a sample from which RNA is extracted to the tank;
applying a magnetic force to the tube in a direction from the first plug to the fourth plug to move a magnetic material from the inside of the tank to the fourth plug;
reverse transcribing the RNA in the reverse transcription reaction solution of the fourth plug to synthesize cDNA; and
releasing the cDNA from the nucleic acid-binding solid-phase carrier in the eluent of the sixth plug.

9. A nucleic acid extraction kit, comprising:
the nucleic acid extraction device according to claim 1;
a nucleic acid-binding solid-phase carrier having a magnetic material; and
a lysis solution for lysing a sample from which nucleic acids are extracted.

10. A nucleic acid extraction kit, comprising:
the nucleic acid extraction device according to claim 2;
a nucleic acid-binding solid-phase carrier having a magnetic material; and
a lysis solution for lysing a sample from which nucleic acids are extracted.

11. A nucleic acid extraction kit, comprising:
the nucleic acid extraction device according to claim 3;
a nucleic acid-binding solid-phase carrier having a magnetic material; and
a lysis solution for lysing a sample from which nucleic acids are extracted.

12. A nucleic acid extraction apparatus, comprising:
a nucleic acid extraction device, which includes a tube that is internally provided with, in the following order from a first end of the tube to a second end of the tube:
a first plug composed of a first oil,
a second plug composed of a first washing liquid, which is phase-separated from an oil and is configured to wash a nucleic acid-binding solid-phase carrier having nucleic acids bound thereto,
a third plug composed of a second oil, a fourth plug composed of a reverse transcription reaction solution, which is phase-separated from an oil and is configured to perform a reverse transcription reaction;

a fifth plug composed of a third oil, a sixth plug composed of an eluent, which is phase-separated from an oil and is configured to elute the nucleic acids from the nucleic acid-binding solid-phase carrier having nucleic acids bound thereto, and a seventh plug composed of a fourth oil; and a magnetic force application device that applies a magnetic force to the tube wherein the device is configured such that the nucleic acid-binding carrier can move from the first plug, through the second, third, fourth, and fifth plugs, and to the sixth plug.

13. The nucleic acid extraction apparatus according to claim 12, further comprising at least one of a magnetic force application device moving unit or a nucleic acid extraction device moving unit, each of which relatively changes a positional relationship between the tube and the magnetic force application device along a longitudinal direction of the tube.

14. The nucleic acid extraction apparatus according to claim 12, further comprising a heating unit which is disposed at a position where the unit heats at least one of the fourth plug or the sixth plug of the tube.

15. The nucleic acid extraction apparatus according to claim 12, wherein the tube is provided with, between the fifth plug and the sixth plug in order from the fifth plug side, a plug composed of a second washing liquid, which is phase-separated from an oil and is configured to wash the nucleic acid-binding solid-phase carrier having nucleic acids bound thereto, and another plug composed of an oil.

16. The nucleic acid extraction apparatus according to claim 12, wherein the eluent contains a DNA polymerase, dNTP, and a primer for the DNA polymerase.

17. The nucleic acid extraction apparatus according to claim 12, wherein the second end of the tube is an open end which is open, and the tube has a detachable stopper which seals the open end.

18. The nucleic acid extraction apparatus according to claim 12, further comprising a tank connectable to the tube and introducing the nucleic acid-binding solid-phase carrier into the tube.

19. The nucleic acid extraction apparatus according to claim 18, wherein the tank and the tube are detachable from each other.

20. The nucleic acid extraction apparatus according to claim 18, wherein the tank contains a lysis solution for lysing a sample from which nucleic acids are extracted.

* * * * *

SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: PCR primer

<400> SEQUENCE: 1
gaccaatcct gtcacctctg ac                                              22

<210> SEQ ID NO 2

```
<211> LENGTH: 24
<212> TYPE: DNA
<213> ORGANISM: Artificial Sequence
<220> FEATURE:
<223> OTHER INFORMATION: PCR primer

<400> SEQUENCE: 2
agggcatttt ggacaaagcg tcta                                              24

<210> SEQ ID NO 3
<211> LENGTH: 24
<212> TYPE: DNA
<213> ORGANISM: Artificial Sequence
<220> FEATURE:
<223> OTHER INFORMATION: Taq man probe

<400> SEQUENCE: 3
tgcagtcctc gctcactggg cacg                                              24
```